(12) United States Patent
Wieters et al.

(10) Patent No.: US 10,481,384 B2
(45) Date of Patent: Nov. 19, 2019

(54) ENDOSCOPE

(71) Applicant: OLYMPUS WINTER & IBE GMBH, Hamburg (DE)

(72) Inventors: Martin Wieters, Barsbuettel (DE); Regina Orzekowsky-Schroeder, Luebeck (DE); Annika Goehring, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/547,293

(22) PCT Filed: Jan. 28, 2016

(86) PCT No.: PCT/EP2016/000142
§ 371 (c)(1),
(2) Date: Jul. 28, 2017

(87) PCT Pub. No.: WO2016/124319
PCT Pub. Date: Aug. 11, 2016

(65) Prior Publication Data
US 2018/0024348 A1 Jan. 25, 2018

(30) Foreign Application Priority Data

Feb. 4, 2015 (DE) .................. 10 2015 101 624

(51) Int. Cl.
*G02B 21/02* (2006.01)
*G02B 23/24* (2006.01)
(Continued)

(52) U.S. Cl.
CPC ...... *G02B 23/2423* (2013.01); *A61B 1/00096* (2013.01); *A61B 1/00163* (2013.01); *A61B 1/00179* (2013.01); *A61B 1/04* (2013.01)

(58) Field of Classification Search
CPC ............ G02B 23/2423; A61B 1/00096; A61B 1/00163; A61B 1/00179; A61B 1/04
(Continued)

(56) References Cited

U.S. PATENT DOCUMENTS

| 4,697,577 A | 10/1987 | Forkner |
| 5,377,669 A | 1/1995 | Schulz |

(Continued)

FOREIGN PATENT DOCUMENTS

| DE | 4211547 A1 | 10/1993 |
| DE | 102008031924 A1 | 1/2010 |

(Continued)

OTHER PUBLICATIONS

English translation of International Preliminary Report on Patentability dated Aug. 17, 2017 together with the Written Opinion received in related International Application No. PCT/EP2016/000142.

(Continued)

*Primary Examiner* — William Choi
(74) *Attorney, Agent, or Firm* — Scully, Scott, Murphy & Presser, P.C.

(57) ABSTRACT

An endoscope having a viewing direction aligned obliquely with respect to a longitudinal axis, the endoscope including: a shaft with a cladding tube and a fiber tube arranged therein; an object lens arranged in the shaft; and a prism module arranged in the shaft for deflecting the beam path, wherein the prism module is arranged eccentrically with respect to the object lens.

11 Claims, 2 Drawing Sheets

(51) Int. Cl.
*A61B 1/00* (2006.01)
*A61B 1/04* (2006.01)

(58) Field of Classification Search
USPC .......................................... 359/656, 726, 737
See application file for complete search history.

(56) References Cited

U.S. PATENT DOCUMENTS

| | | | |
|---|---|---|---|
| 5,601,525 | A | 2/1997 | Okada |
| 5,912,764 | A | 6/1999 | Togino |
| 6,350,234 | B1 | 2/2002 | Foerster-Klein |
| 2002/0091305 | A1 | 7/2002 | Lederer |
| 2010/0016671 | A1 | 1/2010 | Wieters et al. |
| 2013/0030248 | A1* | 1/2013 | Matsumaru ........ A61B 1/00027 600/110 |
| 2013/0310644 | A1 | 11/2013 | Ichimura et al. |
| 2014/0135577 | A1* | 5/2014 | Baumann ........... A61B 1/00096 600/109 |
| 2015/0265137 | A1* | 9/2015 | Takahashi .............. G02B 23/24 600/110 |
| 2015/0289748 | A1 | 10/2015 | Scherr |
| 2017/0071462 | A1* | 3/2017 | Wieters ................. A61B 1/043 |

FOREIGN PATENT DOCUMENTS

| | | |
|---|---|---|
| DE | 102009020262 A1 | 11/2010 |
| DE | 202010017255 U1 | 6/2011 |
| DE | 102012110905 A1 | 5/2014 |
| EP | 2730210 A1 | 5/2014 |
| JP | 01084602 U1 * | 6/1989 |
| JP | H01-084602 U | 6/1989 |
| JP | H05-11196 A | 1/1993 |
| JP | H09-288240 A | 11/1997 |
| JP | H10-090603 A | 4/1998 |
| JP | H10-123411 A | 5/1998 |
| JP | H11-318812 A | 11/1999 |
| JP | 2014-131531 A | 7/2014 |
| JP | 2016-500545 A | 1/2016 |
| WO | WO 01/01186 A1 | 1/2001 |
| WO | 2013-084547 A1 | 6/2013 |

OTHER PUBLICATIONS

International Search Report dated Aug. 2, 2016 issued in PCT/EP2016/000142.
Japanese Office Action dated Jun. 15, 2018 in Japanese Patent Application No. 2017-539005.

* cited by examiner

ENDOSCOPE

CROSS-REFERENCE TO RELATED APPLICATION

The present application is based upon and claims the benefit of priority from PCT/EP2016/000142 filed on Jan. 28, 2016, which claims benefit to DE 10 2015 101 624.9 filed on Feb. 4, 2015, the entire contents of each of which are incorporated herein by reference.

BACKGROUND

Field

The present disclosure generally relates to endoscopes, and more particularly to an endoscope having an oblique viewing direction with a prism module arranged concentrically with respect to an object lens.

Prior Art

Endoscopes facilitate observation of the inside of bodily cavities, which are usually only accessible through small access openings. This involves insertion of a shaft of the endoscope into the hollow space through the opening.

The optical components are typically located at the distal, inserted end of the shaft. They are usually arranged inside a fiber tube, which is surrounded by a casing tube or outer tube. A transport lens system brings the image function to the eyepiece. The image data of a video endoscope can then be transported to an external display device and displayed accordingly.

In endoscopes in which the viewing direction is not parallel but oblique to the longitudinal axis of the shaft, a prism module is provided for deflecting the beam path.

A disadvantage of the known endoscopes is that the size and space requirement of the prism module in the transverse direction relative to the shaft is relatively large. This results from the prism module in the prior art exhibiting a large cross-section in order to enable an adequate image quality.

The illustration of FIG. 1 shows a longitudinal sectional view of a video endoscope 10 known from the prior art.

In this case, however, only one fiber tube 11, which contains the essential optical components, is illustrated. This fiber tube 11 is provided for insertion into an outer tube or cladding tube 12, which is shown here only in phantom. The region between the cladding tube 12 and the fiber tube 11 serves, for example, for receiving optical fibers (not shown here) for illuminating the observation region or field of view.

Cladding tube 12 and fiber tube 11 with the optical components arranged in the interior of the fiber tube 11 form the shaft 13. This is used for insertion into an opening to a bodily cavity that is to be observed, such as, for the area of endoscopic surgery.

Inside the fiber tube 11 of the video endoscope 10, a prism module 14, a lens 15 and an image acquisition unit 16 are arranged as optical components. The object lens 15 is used here to image the area or field of view to be observed on the image acquisition unit 16. An image sensor or video sensor, for example a CCD sensor or a CMOS sensor, can be used as the image acquisition unit 16. The object lens 15 provides a corresponding optical image on a light-sensitive region of the image acquisition unit 16. Evaluation electronics (not shown here) are generally arranged outside the endoscope 10 and connected to the video endoscope 10 by means of a cable connection (likewise not shown).

The video endoscope 10 illustrated in FIG. 1 is a so-called "oblique-looking video endoscope." This means that the observation direction is not aligned in the direction of the longitudinal axis of the video endoscope 10, but rather obliquely to the longitudinal extent of the video endoscope 10 or its shaft 13. The object lens 15 and the image acquisition unit 16 are already parallel to the longitudinal axis of the video endoscope 10 or of the shaft 13 with the fiber tube 11 or the cladding tube 12 for reasons of space. This in principle ensures a compact, linear structure so as to simultaneously minimize the cross-sectional dimensions of the video endoscope 10.

However, the region to be observed does not lie in the direction of the longitudinal axis, but obliquely thereto and away from the axis. Accordingly, in order to allow for a deflection of the beam path from the region to be monitored onto the object lens 15 or the image acquisition unit 16, the prism module 14 is required.

The prism module 14 typically comprises two interconnected individual prisms 17 and 18. The two prisms 17 and 18 are connected to one another at a connection point 19, generally by means of adhesion. The adhesive site is realized by means of an optical adhesive for adjustment of the refractive indices at the connection point 19. Thus, sufficient reflection at the connecting point of the prisms 17 and 18 is made possible. This leads to a sketched beam path 20 with a reflection on the upper side edge of the prism 18 and on the connecting plane 19.

The video endoscope 10 of FIG. 1 shows that the lower region of the prism module 14 makes a virtually insignificant contribution to the optical image on the image acquisition unit 16. That's because the beam path 20 essentially runs in the upper region of the prism module 14 in the illustration. Thus, the lower region of the prism module 14 is in practice not decisive for the optical quality of the image.

In FIG. 4, a known video endoscope 10 is shown, in which the prism module 14 is aligned centrally with the fiber tube 11. Here, the prism module 14 extends over the entire inner cross-section 24 of the fiber tube 11. The optical path 20 consequently runs primarily centrally with the fiber tube 11. This allows for a corresponding image to be produced by the object lens 15 on the image acquisition unit 16, which essentially corresponds to the cross-section of the prism module 14.

SUMMARY

The endoscopes described herein can either be of the type of lens endoscopes or video endoscopes. Lens endoscopes contain an eyepiece in the lens system for transport and display on an eyepiece. In the case of a video endoscope, an image sensor of the shaft provides an image taken behind an object lens to produce video camera pictures.

It is an object to provide an endoscope, which allows for smaller later dimensions or cross-sections of the prism module.

Such object can be achieved by an endoscope in which the prism module is arranged eccentrically with respect to the object lens, thus, not central or centered. In conventional endoscopes, however, the prism module is aligned centrally with the object lens. However, due to the radiation course, this is not necessary. Instead, a structural shape of the prism module with a comparably reduced cross-section is used. This therefore has smaller cross-sectional dimensions. By means of an eccentric arrangement with respect to the object lens, the overall cross-section of the prism module can be reduced.

The prism module can be arranged eccentrically with respect to the cross-section of the shaft or the fiber tube. At the same time, the cross-section of the prism module can be reduced in comparison with the prior art. The cross-section of the fiber tube can be simultaneously maintained or also reduced. In this way, free space is created in the region between the prism module and the shaft or fiber tube, or the cross-sectional dimensions of the fiber tube are also reduced.

The object lens and/or possibly the image acquisition unit can be arranged eccentrically with respect to the cross-section of the shaft or of the fiber tube. Accordingly, free space may result between the lens or the image acquisition unit and the fiber tube or the shaft. The distance between fiber tube and prism module can be only present on one side or can be larger on one side than on the opposite side. This creates space in the area between the prism module and the fiber tube or shaft in the respective interior space.

The outer cross-section of the prism module can be smaller than the inner cross-section of the shaft or of the fiber tube. Due to the fact that the prism module does not occupy the complete cross-section of the shaft or fiber tube, free space is created in the intermediate region. An eccentric arrangement of the optical components, such as the prism module of the image acquisition unit or the lens, is thereby made possible. The cross-section of the prism module, perpendicular to the longitudinal direction of the endoscope, can be smaller than the internal cross-section of the fiber tube or the shaft. In this way, the reduction takes place in the part of the prism module that is practically irrelevant for the image transmission. A hollow space can be provided in the shaft, such as, in the region between the prism module and the inner wall of the fiber tube. This can be a crescent-shaped hollow space. As a result, an at least substantially arcuate or round external shape of the prism module does not fill the entire internal cross-section of the fiber tube or of the shaft. Depending on the outer shape of the prism module and the inner cross-section of the fiber tube or the shaft, however, other forms of the resulting free space or hollow space can also result.

At least one component can be arranged between the prism module and the inner wall of the shaft or of the fiber tube, in particular in the hollow space. Such component can be an electrical and/or electronic component. At this point, various elements can be provided, for example active and/or passive components. Such components can be measuring devices, measuring sensors or the like. Such components can also be mechanical components.

At least one heating element can be arranged between the prism module and the inner wall of the shaft or of the fiber tube, such as in the hollow space. Alternatively, a cooling element can be similarly arranged. A heating foil and/or at least one heating wire can be used as the heating element. If desired, a Peltier element or the like can also be provided. Heating elements can serve to prevent fogging of the optical components by condensing water. A suitable temperature control, such as by means of heating, can be required for this purpose.

At least one temperature sensor can be arranged between the prism module and the inner wall of the shaft or of the fiber tube, such as in the hollow space. The temperature sensor can be a thermistor. This allows for temperature measurement in the region of the prism module. A temperature sensor can be used to determine the current temperature. The temperature sensor can serve to carry out temperature measurements and/or temperature control and/or prevent overheating, for example in the case of heating, by means of a heating element.

The prism module can comprise a plurality of prisms, such as at least two prisms assembled to make up the prism module. Such a configuration facilitates a deflection of the beam path. The prism module can be configured for rotating and/or tilting or for generally deflecting the beam path.

BRIEF DESCRIPTION OF THE DRAWINGS

Exemplary embodiments are described in more detail below with reference to the drawings, which.

DETAILED DESCRIPTION

Figure 1:
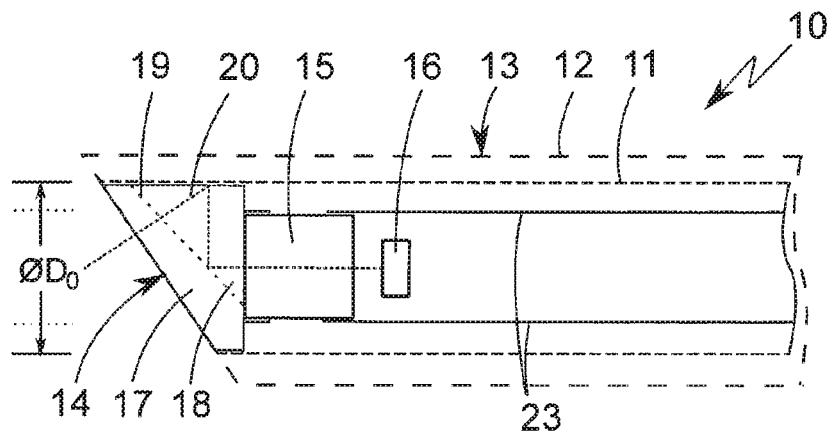
FIG. 1 illustrates a longitudinal section of a shaft of a video endoscope according to the prior art.
Figure 2:
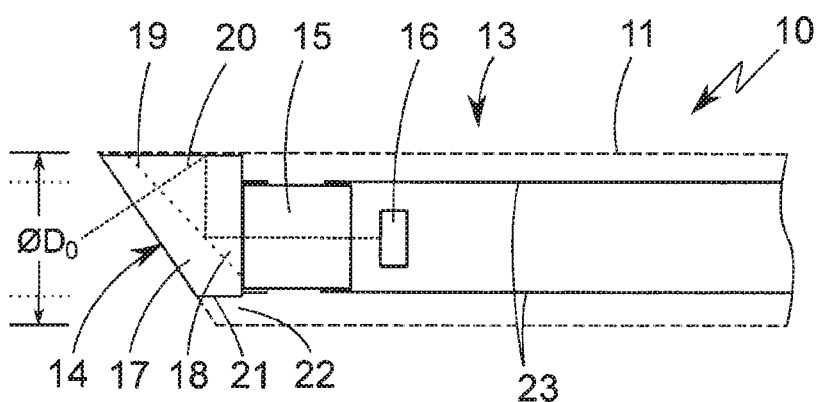
FIG. 2 illustrates a longitudinal section of a shaft of a video endoscope in accordance with a first exemplary embodiment.

The video endoscope 10 of FIG. 2, unlike the known video endoscope 10 of FIG. 1, includes a prism module 14 which is reduced in diameter or cross-section and is configured to be axially offset (note that the outer tube or cladding tube 12 is not shown in FIG. 2). The lower wall of the fiber tube 11 is correspondingly spaced from the lower edge of the prism assembly 14. For this purpose, the transverse dimensioning of the prism module 14 in the vertical direction of the drawing plane was compared with the diameter $D_0$ of the fiber tube 11.

Thus, a hollow space 22 is formed in the region between the lower edge 21 of the prism module 14 and the wall of the fiber tube 11. This hollow space 22 can remain free, or different components can be arranged therein. For example, a heating element (not shown here) or another component or part can be provided. For example, a measuring device such as a thermistor or the like can be used.

The prism module 14 is consequently oriented eccentrically to the fiber tube 11 in this case. Since the beam path continues to pass centrically to the fiber tube 11, the object lens 15 with the image acquisition unit 16 and the surrounding object lens tube is aligned centrally with the fiber tube 11 as in the prior art.

Accordingly, the beam path 20 essentially extends centrally to the fiber tube 11. Only the prism module 14 is thus arranged eccentrically or decentrically, i.e. with the optical axis corresponding to the beam path, but with its cross-section decentered thereto.

Figure 3:
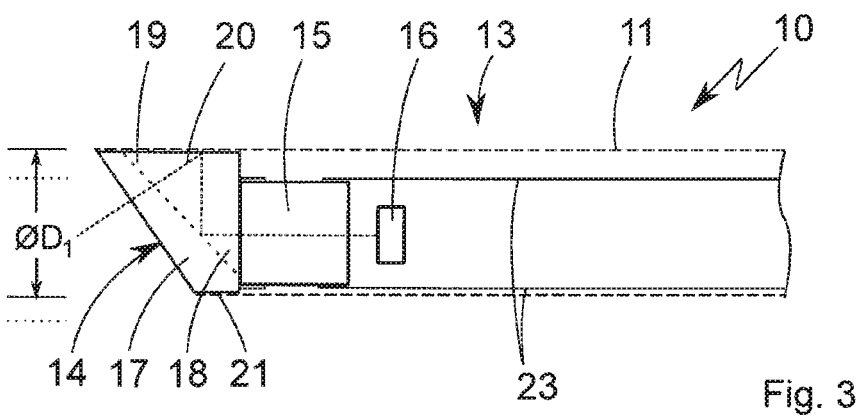
FIG. 3 illustrates a longitudinal section of a shaft of a video endoscope in accordance with a second exemplary embodiment.
Figure 4:
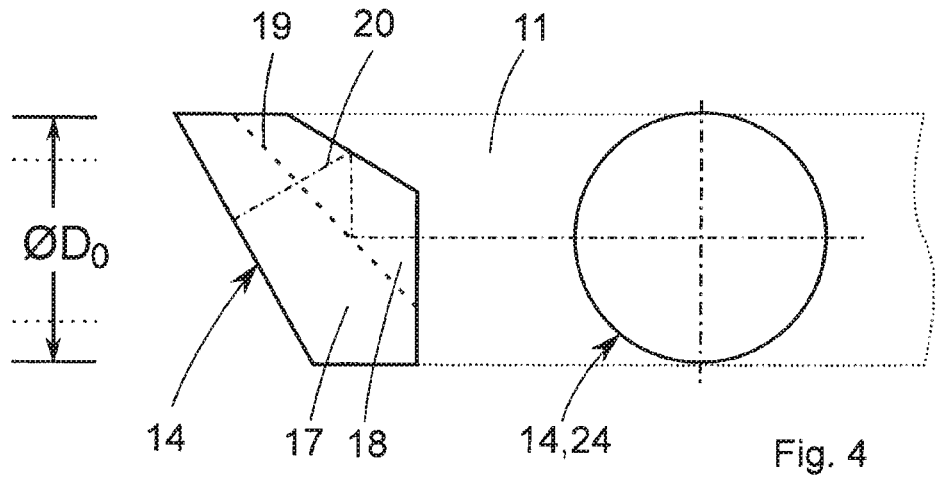
FIG. 4 illustrates a schematic representation of the beam path in a video endoscope according to the prior art of FIG. 1.

In the second exemplary embodiment of the invention according to FIG. 3, a prism module 14 reduced in diameter or cross-section can be used.

However, in this case, the cross-section of the fiber tube 11 has also been reduced. Thus, the outer diameter $D_1$ of the fiber tube 11 has been reduced in comparison to the known solution of FIG. 1. In this case, an additional hollow space 22 is not produced at all or only to a small extent.

In the exemplary embodiment of FIG. 3, the prism module 14 is aligned centrally with respect to the fiber tube 11. The object lens 15 with the image acquisition unit 16 is aligned with the surrounding system tube 23 decentrally to the fiber tube 11. This ensures that the beam path can enter the object lens 15 and the image acquisition unit 16 centrally. As a result, however, the prism module 14 and the object lens 15 are aligned eccentrically with respect to one another.

Figure 5:
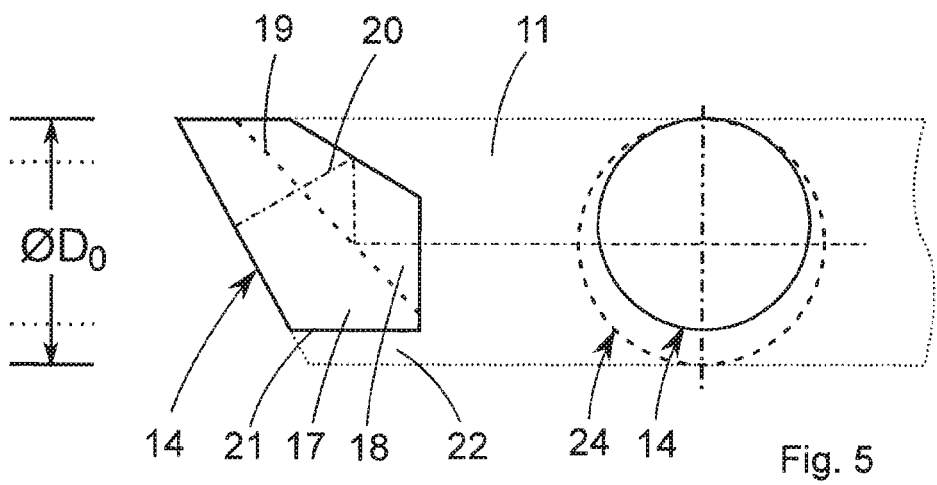
FIG. 5 illustrates a schematic representation of a beam path of a video endoscope in accordance with the exemplary embodiment of FIG. 2.
Figure 6:
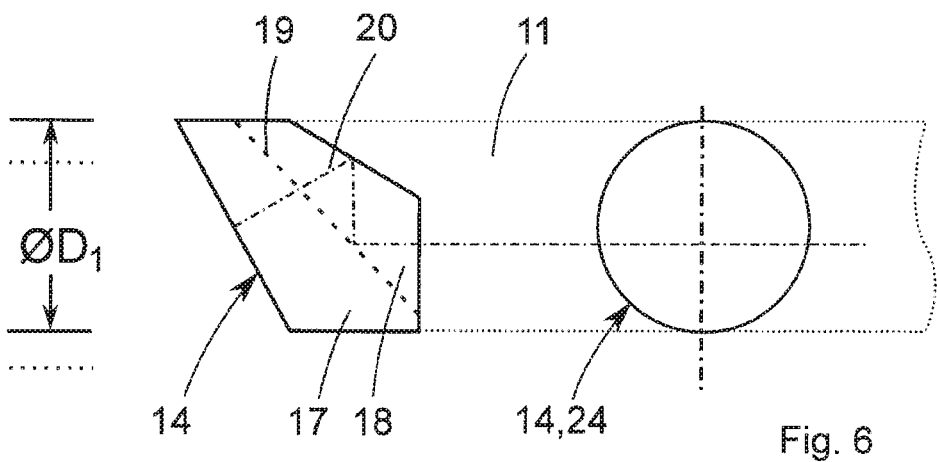
FIG. 6 illustrates a schematic representation of a beam path of a video endoscope in accordance with the exemplary embodiment of FIG. 3.

In FIGS. 5 and 6, corresponding beam paths 20 with sketched cross-sections 24 of the respective prism module 14 are shown in a front view according to FIGS. 2 and 3.

In FIG. 5, which corresponds with the exemplary embodiment of FIG. 2, a prism module 14, which is reduced in cross-section 24, is provided. The prism module 14 has a cross-section that is smaller than the cross-section of the fiber tube 24 represented here by dashed lines. In this case, the prism module 14 is arranged in the upper region of the fiber tube 11. Consequently, a hollow space 22 for installing additional structural elements 22a is formed in the lower region. Such structural elements can include electrical and/or electronic components, measuring devices, measuring sensors, and heating or cooling elements.

The illustration of FIG. 6 corresponds to the second exemplary embodiment of FIG. 3. Due to the reduction, also of the cross section 24 of the fiber tube 11, the prism module 14 on the other hand occupies the entire cross-section of the fiber tube 11. The corresponding gain in space is achieved by a reduction of the outer cross-section of the fiber tube 11 and possibly also of the entire shaft 13 with the envelope tube 12.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Video endoscope
11 Fiber tube
12 Cladding tube
13 Shaft
14 Prism module
15 Object lens
16 Image acquisition unit
17 Prism
18 Prism
18 Connection level
20 Beam path
21 Lower edge
22 Hollow space
22a Structural elements
23 Lens tube/system pipe
24 Cross-section

What is claimed is:

1. An endoscope having a viewing direction aligned obliquely with respect to a longitudinal axis, the endoscope comprising:
a shaft with a cladding tube and a fiber tube arranged therein;
an object lens arranged in the fiber tube; and
a prism module arranged in the fiber tube for deflecting a beam path, wherein the prism module is arranged eccentrically with respect to the object lens;
wherein an outer cross-section of the prism module is smaller than an inner cross-section of the fiber tube, a cross-section of the prism module being less than the inner cross-section of the fiber tube such that a hollow space is provided in a region-between the prism module and an inner wall of the fiber tube; and
at least one component is arranged between the prism module and the inner wall of the fiber tube or in the hollow space.

2. The endoscope according to claim 1, wherein the prism module is arranged eccentrically to a cross-section of one of the shaft or the fiber tube.

3. The endoscope according to claim 1, wherein the object lens is arranged eccentrically to a cross-section of one of the shaft or the fiber tube.

4. The endoscope according to claim 1, wherein the at least one component is at least one heating element arranged between the prism module and the inner wall of the fiber tube or in the hollow space.

5. The endoscope according to claim 4, wherein the at least one heating element is a heating foil or a heating wire.

6. The endoscope according to one claim 1, wherein the at least one component is at least one temperature sensor, is arranged between the prism module and the inner wall of the fiber tube or in the hollow space.

7. The endoscope according to claim 6, wherein the at least one temperature sensor is a thermistor.

8. The endoscope according to claim 1, wherein the prism module comprises a plurality of prisms.

9. The endoscope according to claim 8, wherein the plurality of prisms comprises first and second prisms.

10. The endoscope according to claim 1, wherein the hollow space has a crescent shape.

11. The endoscope according to claim 1, wherein the at least one component is an electrical component.

* * * * *